United States Patent [19]

Frank et al.

[11] Patent Number: 4,877,399
[45] Date of Patent: Oct. 31, 1989

[54] DENTAL EQUIPMENT CLEANING APPARATUS AND METHOD

[75] Inventors: Glenn R. Frank, New Fairfield; Edward T. Stewart, Jr., New Milford, both of Conn.

[73] Assignee: Robert Thomas Ltd., Media, Pa.

[21] Appl. No.: 205,735

[22] Filed: Jun. 13, 1988

[51] Int. Cl.⁴ .............................................. A61C 1/05
[52] U.S. Cl. ....................................... 433/25; 433/132
[58] Field of Search ................. 433/137, 114, 132, 25

[56] References Cited

U.S. PATENT DOCUMENTS 3,494,110  2/1970  Reed et al. ........................... 433/114

Primary Examiner—Robert Peshock
Attorney, Agent, or Firm—Stuart S. Bowie

[57] ABSTRACT

Method and apparatus for cleaning clogged dental equipment lines, such as water and air lines and drains, for a wide variety of dental equipment such as cuspidors and handpieces. One embodiment has an air hose connected to a connector for a handpiece for a drill, etc., wherein the connector has an interior plastic insert which closes off air to the holes in the drill for drive and exhaust air and allows air through two holes which connect with the spray air and water ports of the handpiece for the drill whereby the air blows out the clogged slits. Another embodiment uses the air hose with a rubber nozzle to blow clogged suction lines. Another embodiment has a rubber element with a hole in its middle which fits over the discharge hole in the cuspidor, whereby the air blows out the debris clogging the cuspidor hole and connecting lines.

2 Claims, 4 Drawing Sheets

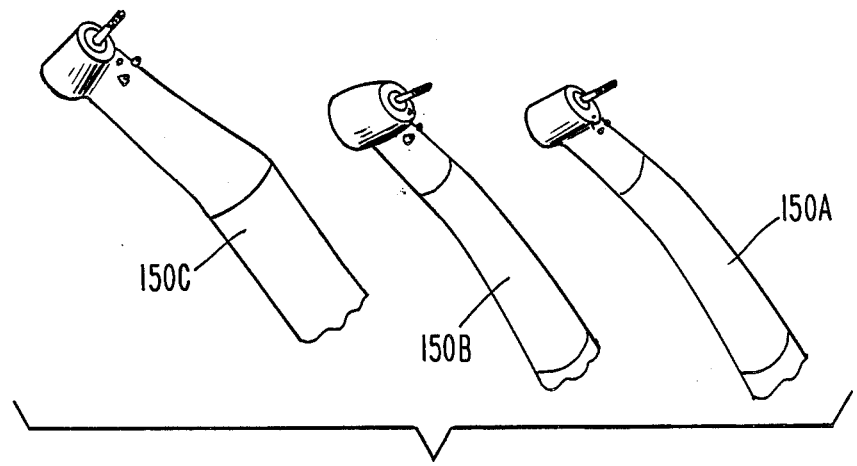
Fig. 1
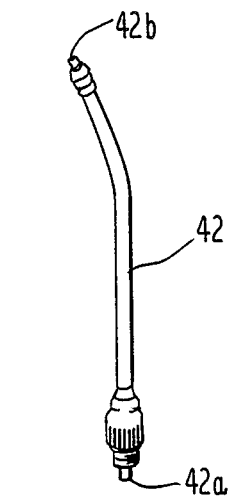
Fig. 2
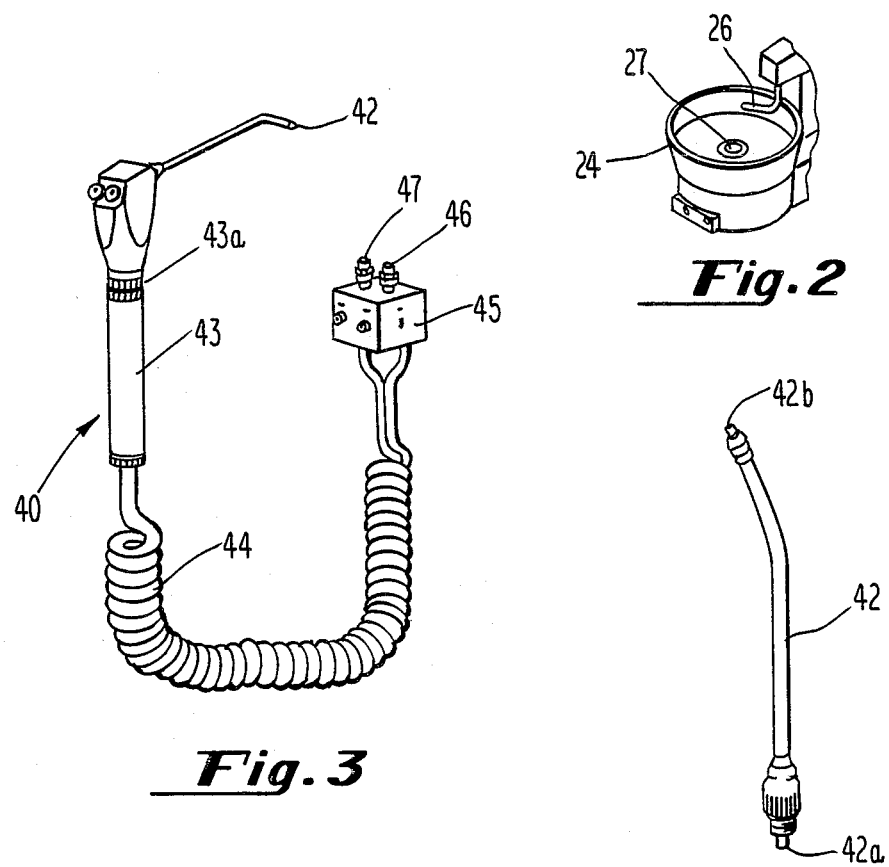
Fig. 3
Fig. 4

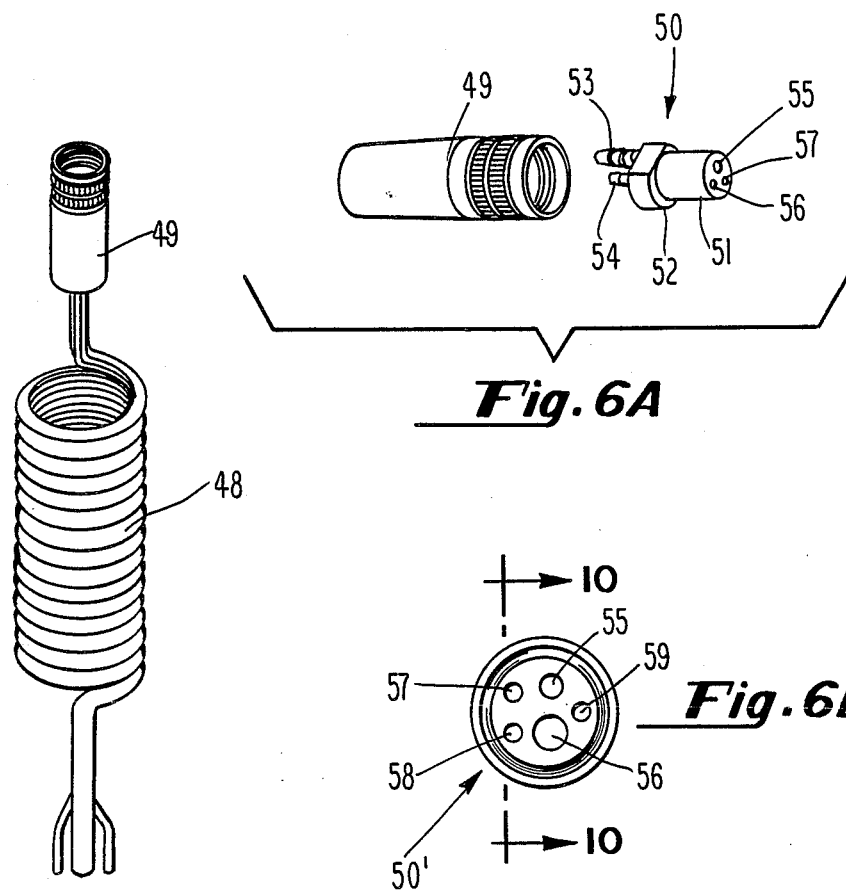

DENTAL EQUIPMENT CLEANING APPARATUS AND METHOD

BACKGROUND

Modern dental offices are equipped with a variety of instruments for cleaning, drilling and performing other tasks relating to the teeth and gums of patients.

Typically, air under pressure is used to drive the "turbines" of drills and similar devices. Additionally, water is injected under pressure into the mouth to clean debris and the debris and water are removed via suction tubes. Also, cuspidors are employed whereby the patient periodically spits out accumulated water and debris.

A significant problem with all of these systems is that the debris, which includes metal fragments, amalgam and other hard matter quickly clog up the tubes and holes and slits of the devices employed.

At present, the only solution for removing clogging of drill handpieces is to send them back to the manufacturer who disassembles and cleans them, In this regard, it might be noted that drills, jets for emitting abrasives (such as those sold as "Prophy Jet" by Dentsply International, Inc.) etc., are often sold with thin wires, but these are generally ineffective to remove clogs, especially those which are far into the device and inaccessible to such wires. Even when cleaning of such equipment can be done in the office, a service technician is employed.

The failure of dental equipment occurs at various intervals and depends on the specific instrument and degree of use. However, clogging occurs with many devices quite often. When the clogged equipment is essential to the ability of the operatory to function, e. g., the cuspidors of suction lines, the dentist must shut down his/her entire system until the units are cleaned, which downtime is tremendously expensive for the dentist.

SUMMARY

The present invention provides methods and apparatus for cleaning dental equipment in the dentist's office by the dentist or his/her employees.

Moreover, this cleaning system can be accomplished quickly, usually in a matter of minutes, so that the equipment can be restored to use without undue delay, thereby avoiding costly downtime.

In one aspect, the invention provides a novel insert which is contained in a fitment, which insert has holes for communicating with the water and spray holes of a handpiece or similar device, but which closes off the channels normally used to pass the turbine drive air and exhaust air for the drill, etc. This insert is fitted to an air pressure hose which, in turn, is connected to the pressurized air supply of the office.

In another embodiment, the invention provides methods and apparatus for cleaning suction tubes. The suction tubes used to remove water and debris from the patient's mouth become clogged very often. This is a serious problem for the dentist, since he/she must hire a serviceperson to blow out the debris, etc. clogging the lines. Since it is usually not possible to know where the clogging is, the debris is often blown throughout the dentist's patient treatment room, which, among other things, unsanitary and thus highly undesirable.

Another embodiment is a method for cleaning cuspidors which become clogged with debris which is spit into them by the patient. Such cuspidors use gravity drain lines and this invention employs a special sealing member with an opening concentric with the discharge opening in the cuspidor and a fitment on the end of the pressurized air gun which fits snugly into the hole of the member, whereby pressurized air is used to blow out the clogging materials.

The foregoing summarizes not only the primary various embodiments of the invention, but also serves to convey the objects of the invention which are, as indicated, to provide method and apparatus for cleaning a variety of dental equipment in the dentist's office without undue delay and very inexpensively compared to existing techniques.

THE DRAWINGS

FIG. 1 is an enlarged perspective view of various types of drill handpieces of the type found in modern dentist's offices.

FIG. 2 is a perspective view of a cuspidor unit found in dentist's offices.

FIG. 3 is a perspective view of an air/water syringe typically found in a modern dentist's office. part of the assembly in FIG. 1.

FIG. 4 is a perspective view of the syringe tip shown in FIG. 3, but from another angle.

FIG. 5 is a perspective view of an air pressure hose connected to a connector for a drill, etc.

FIG. 6A is an exploded view in perspective of the coupling of FIG. 5, shown on the left, and an insert for air and water which fits into the coupling, shown on the right.

FIG. 6B is a frontal view of one type of conventional insert of the kind generally shown in FIG. 6A.

FIG. 6C is a front view of another standard insert of the kind generally shown in FIG. 6B.

DETAILED DESCRIPTION

Figure 7:
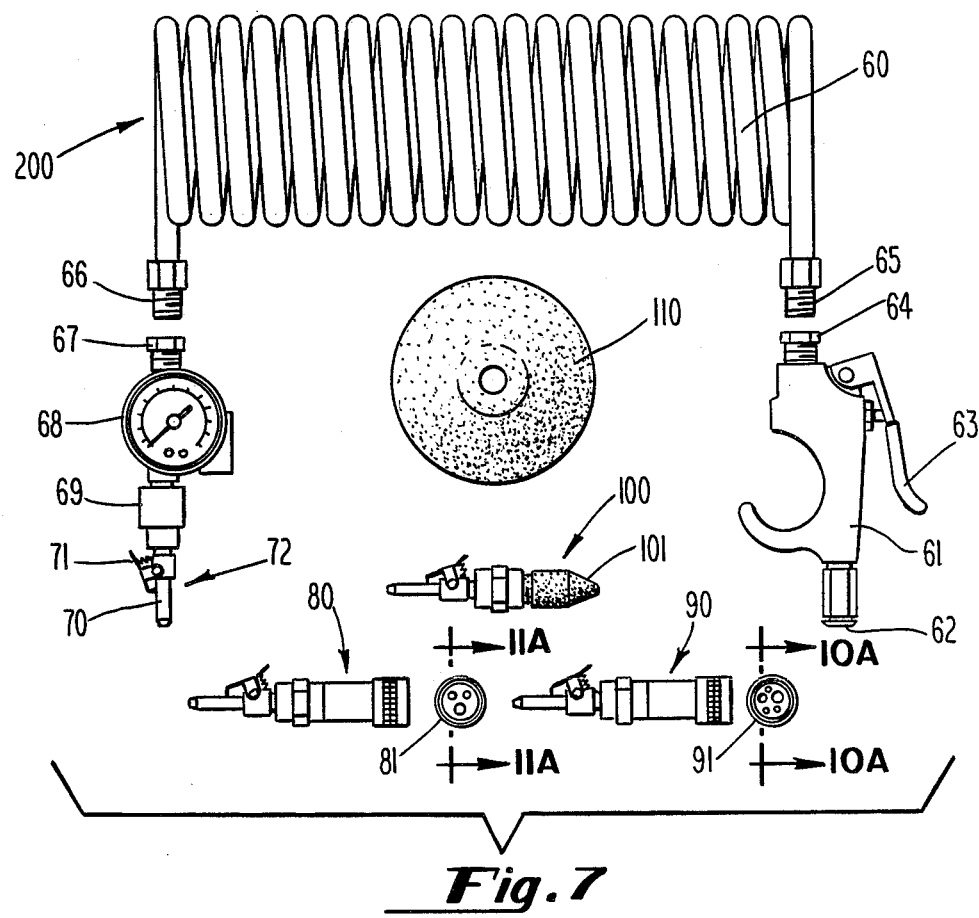
FIG. 7 is an perspective view of the various components of the present invention unconnected to each other.

FIG. 1 illustrates several types of drill handpieces used in modern dentist's offices.

Modern dental offices have high speed drill handpieces 150, 151 which are fed by air pressure hoses supplied by the a pressure unit. The drills 150, 151 also have water pressure lines (not shown) fed within lines the pressure hoses, so that water and air can be injected onto the teeth during drilling. As indicated, FIG. 1 shows in enlarged detail handpieces 150A-C. representative of the various types of handpieces shown in FIG. 1.

Connectors 15 and 16 connect drills 150, 151 to the lines 48,48'.

In addition, there is saliva ejector valve 42 connected to a suction tube for removing debris and water from the mouth, as well as a high volume evacuation valve (HVE) connected to a suction tube (not shown). Also shown in FIG. 3 is a air/water syringe 40 connected to a suction hose 44.

FIG. 2 shows in somewhat larger detail the cuspidor 14. As explained, when the patient ejects water and debris into the cuspidor 24, the same are conveyed through the discharge hole 27 which is connected to a drain line. The cuspidor opening 27 and the drain line (not shown) frequently become clogged with the debris and, when this occurs, a service person must usually be hired to disassemble the unit at significant cost, loss of the unit—and, consequently, substantial lost income to the Dentist.

FIG. 3 depicts a syringe tip 42 for air and water connected to a housing 43a. The latter is connected to a handle 43 which, in turn, is connected to a hose 44 which terminates in a block 45 having fittings 46, 47. This assembly as a whole is referred to as 40. The tip 42 is shown from a different angle is FIG. 4.

Figure 12:
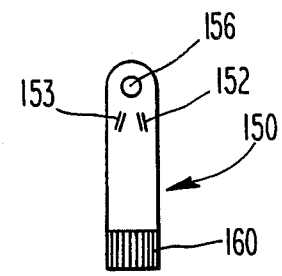
FIG. 12 is a view in perspective of a drill handpiece of the type shown in FIG. 1.

Handpiece 150, shown in FIG. 12, has a coupling 160 which can be fitted into a connector 49 which is fed by an air pressure tube 48, as shown in FIG. 5. Connector 49 is shown in FIG. 6A at the left. To the right in FIG. 6A is shown a standard insert 50 which is placed inside connector 49. Insert 50 has two ports, 53, 54, one for air and the other for water, which connect with holes 56, 57. Drive air for the drill handpiece turbine is supplied through a port 55, as shown in FIG. 6C.

FIG. 6B illustrates another insert 50' with channels 40 designating the turbine drive air and 58 the spray air and 57 the spray water for the drill. 56 is for exhausting the drive air and 59 is for an optical fiber.

Inserts 50 and 50' are standard equipment today and it will be understood that each of the channels or holes described communicate through connector 49 to the air pressure unit for the handpieces 150, 151.

However, turning to the handpiece 150 shown in FIG. 12, in addition to the chuck 156 for holding the drill bit, there are two slits, 153 for injecting water served by channel 58 and slit 152 for injecting air, served by channel 57, and these two slits frequently become clogged with debris, etc. The handpiece 150 is attached to coupling 49 by means of a connector 160.

Thus, when slits 152, 153 become clogged, the present invention provides a quick means for unclogging the slits in the office.

Figure 11:
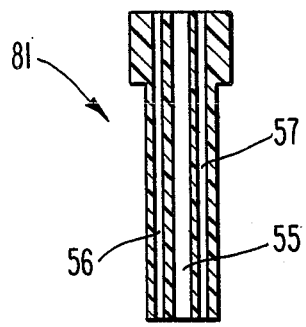
FIG. 11 is a sectional view taken along the lines 11—11 of FIG. 6C of a conventional insert.
Figure 11A:
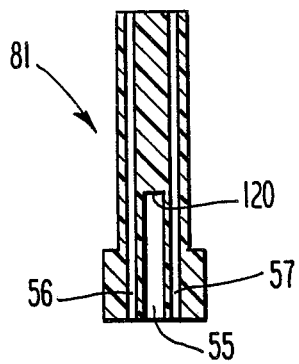
FIG. 11A is a sectional view taken along the lines 11A—11A in FIG. 4 showing another insert of this invention.
Figure 13:
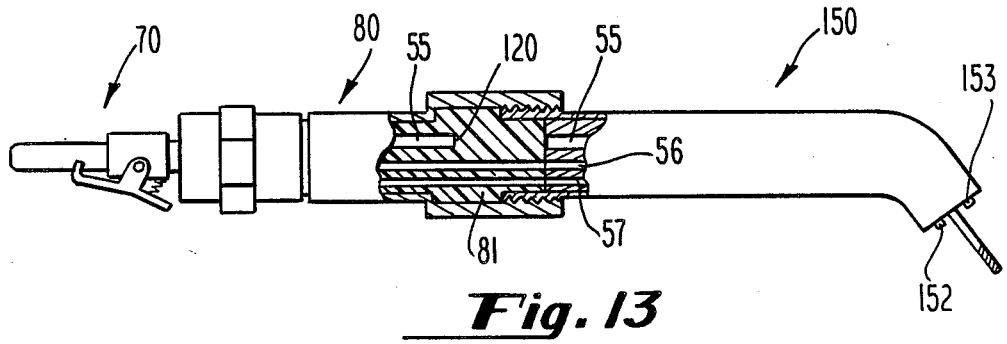
FIG. 13 is a side elevation partly in section, of one of the adapters of the invention illustratively connected to a dental handpiece.

This is accomplished by attaching an adaptor 80 (for a three hole insert as shown in FIG. 7) or 90 (for a four hole insert shown in FIG. 7. Adaptor 80 contains a novel insert 81 which, as shown in FIG. 11A has the turbine air passage 55 closed at 120. This attachment of adapter 80 to handpiece 150 is clearly shown in FIG. 13, wherein channels 56, 67 of adapter 80 are so aligned with and communicate with the like-numbered channels in handpiece 150. However, channel 55 in adapter 80 is closed or blocked at 120 by the material of the adapter, so that it does not communicate with the channel 55 of the handpiece 150. Similarly, insert 91 has air passage 58 closed at 121 and air exhaust passage 56 blocked at 122.

Thus, in the case of a three hole handpiece, adapter 80 with insert 81 within it, is connected to an opening 62 of an air gun 61 which has a quick release handle or level 63.

Pressurized air from the pressure air supply in the dentists' office is connected by a female connector (not shown) which connects with male connector 72. Connector 72 has a block 69 at the top which receives an air gauge 68. At the top of gauge regulator assembly 68, there is a screw coupling 67 which receives a threaded coupling 66 which is at the input end of air pressure hose 60.

The unit 200 (i. e., the system from member 70 to 62 shown in FIG. 7) is designed to be sold preassembled for ready use by the Dentist and/or his/her technician. It is important that the air pressure be properly set by means of regulator assembly 68. A pressure of 30 psi or less is currently required by OSHA regulations, and this pressure will accomplish the functions of this invention.

The Dentist or assistant then attaches one of the handpiece adaptors 80, 90 or 100 to coupling 62.

When the pressure is correct, the handle 63 is depressed and the pressurized air flows through the system described and blows the clogged debris, etc., through the handpiece 150 and finally out of the slits 152 and 153.

As mentioned, the syringe 40 shown in FIG. 3 frequently becomes clogged. In the case where syringe tip 42 is clogged, syringe tip 42 is removed from housing 43a and conical rubber tip 101 is pressed firmly against either orifice 42a or 42b of tip 42 and the tip 42 is blown free of debris.

Figure 8:
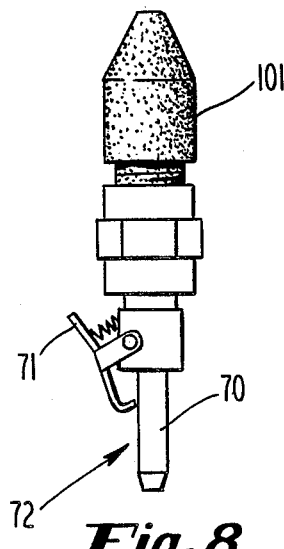
FIG. 8 is a perspective view of a conical cleaning tip of this invention attached to a quick release connector.
Figure 9:
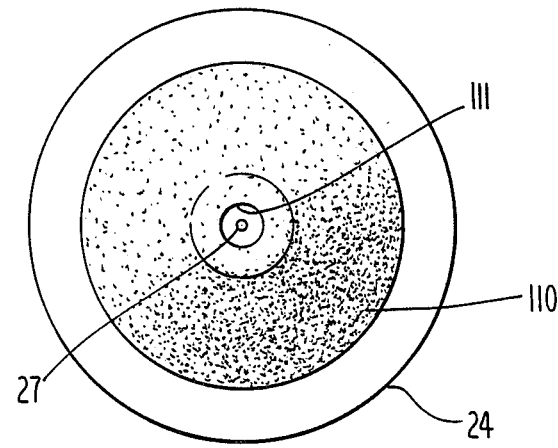
FIG. 9 is a top view of the cuspidor adaptor of this invention shown in FIG. 7 placed over the cuspidor shown in FIG. 1.
Figure 10:
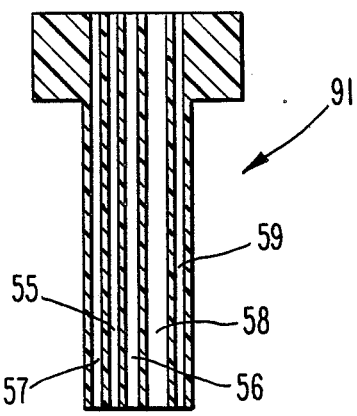
FIG. 10 is a sectional view taken along lines 10—10 of FIG. 6B of a conventional insert.
Figure 10A:
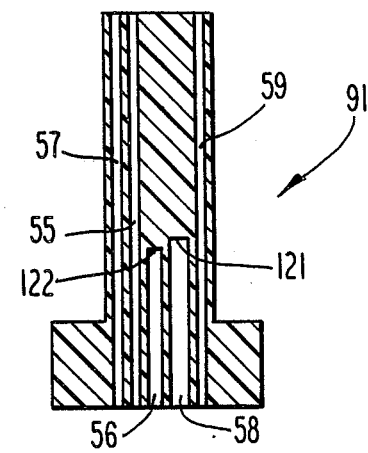
FIG. 10A is a sectional view taken along the lines 10A—10A of the right hand insert shown in FIG. 7B showing one embodiment of the insert of this invention.

When cuspidor 24 becomes clogged, conical cleaning tip 101, which is preferably rubber and which has a central channel with an opening at the tip (not shown) and which is preferably pre-fitted to adaptor 72 is fitted to coupling 62 as shown in FIG. 8. Then the adapter 101, preferably rubber, is placed in the middle of cuspidor 24 so that the hole 111 in the adapter is concentric with the discharge outlet 27 of the cuspidor.

Tip 101 is then placed tightly into hole 111 of adaptor 110, handle 63 is squeezed to allow air to pass under pressure through the orifice of tip 101, and consequently, the high air pressure blows out the debris in the drain system.

The foregoing illustrates how many types of equipment in dental offices may be cleaned with the method and apparatus of this invention. Other equipment which can be cleaned as described include operatory sinks, hoses prophy jets, cavi endo units, cavitrons, water lines, handpiece lines and syringe tips. Indeed, the equipment may be generally classified as any which have a coupling to receive the pressurized air system of this invention.

We claim:

1. For use in combination with an air driven turbine-type dental handpiece, wherein the handpiece has an upper portion containing the turbine, a first opening for receiving a drill or other dental instrument, and a lower portion terminating in connecting means, and wherein said handpiece has an internal channel for transmitting drive air to the turbine extending from said turbine to said connecting means, and cleaning water and cleaning air channels extending internally within said handpiece from openings adjacent said first opening to said connecting means, the improvement comprising, an adapter for removing debris from said cleaning water and cleaning air channels within said handpiece, said adapter having:

(a) a fitting having means for connecting the fitting to said connecting means of the handpiece;

(b) an insert positioned within said fitting, said insert having means for blocking the flow of drive air to the handpiece, said insert also having first and second channels respectively aligned to communicate with said cleaning water and cleaning air channels of said handpiece, and, (c) means for introducing pressurized air into said fitting and into said first and second channels thereof and thence through said cleaning water and cleaning air channels of said handpiece, whereby said pressurized air removes debris from said cleaning water and cleaning air channels of said handpiece.

2. A method of cleaning dental turbine handpieces having an internal channel for air to drive the turbine and at least one air internal channel which becomes clogged with debris, comprising the steps of closing the turbine air channel by using an adapter means with an insert means for blocking the flow of drive air and having channels to communicate with cleaning water and cleaning air channels of the handpiece and introducing air under pressure through the said clogged channel to remove the clogging material.

* * * * *